United States Patent [19]

Mathews

[11] 4,282,877
[45] Aug. 11, 1981

[54] HAIR REMOVING ARRANGEMENT

[75] Inventor: Larry Mathews, New York, N.Y.

[73] Assignee: Alleghany Pharmacal, New York, N.Y.

[21] Appl. No.: 15,221

[22] Filed: Feb. 26, 1979

[51] Int. Cl.³ .............................................. A61B 17/00
[52] U.S. Cl. ........................................ 128/355; 8/160
[58] Field of Search ..................... 128/355; 8/160, 161

[56] References Cited

U.S. PATENT DOCUMENTS

| 1,620,539 | 3/1927 | Gernsback | 128/355 |
| 2,326,609 | 8/1943 | Borglin | 8/160 |
| 2,377,774 | 6/1945 | Gotham | 8/160 |
| 2,425,696 | 8/1947 | Herrmann et al. | 128/355 X |
| 2,954,324 | 9/1960 | Brummer | 128/355 |
| 3,470,877 | 10/1969 | Morgan | 128/355 |

Primary Examiner—Dalton L. Truluck
Attorney, Agent, or Firm—Steinberg & Raskin

[57] ABSTRACT

The invention relates to an arrangement for removing unwanted hair and to a method of effecting such removal. Strips of sheet material of predetermined size and shape having a pressure sensitive adhesive and wax depliatory on one face thereof are placed in contact with the unwanted hair and then pulled away therefrom, removing the unwanted hair therewith.

4 Claims, No Drawings

HAIR REMOVING ARRANGEMENT

BACKGROUND OF THE INVENTION

Selective hair removal, for example for the shaping of eye brows, is very difficult and can be painful.

This is generally accomplished by tweezing or plucking because the use of depilatories is too difficult to control for use where shaping of the hair line is desired.

Attempts have been made to use hot wax for hair removal and shaping. This, however, can be painful and in addition requires professional application.

SUMMARY OF THE INVENTION

Generally speaking in accordance with the present invention, a pressure sensitive adhesive in applied to a face of a sheet material of predetermined shape. The adhesive composition includes a high molecular wax-like substance. The sheet material is applied in the desired shape and at the desired place to the area from which undesired hair is to be removed and pressed against the same. The adhesive with the high molecular substance therein adheres firmly to the hair and a quick peeling motion of the strip results in the removal of the hair which adheres to the adhesive on the sheet material.

It is accordingly a primary object of the present invention to provide an arrangement which can be used for the removal of unwanted hair in selected spots without the removal of wanted hair.

It is another object of the present invention to provide an arrangement for removing unwanted hair and shaping hair line under controlled conditions with minimum pain and without removal of wanted hair.

It is yet a further object of the present invention to provide a method and composition for achieving the removal of hair and the shaping of hair line.

Other objects and advantages of the present invention will be apparent from further reading of the specification and of the appended claims.

With the above and other objects in view, the present invention mainly comprises shaped strips of sheet material having a pressure sensitive adhesive composition applied to a face thereof, said composition including a high molecular substance, the composition adhering more firmly to hair than to skin so that when the material is applied to the hair and skin and then pulled from the same only hair is removed.

The sheet material may be of plastic, paper, cellophane, etc. In accordance with the invention the sheet material is made in various sizes and shapes with curves in different places, inward curves, outward curves, etc. so that the different pieces of the sheet material can be applied to different areas. For example, pieces of sheet material having an outward curve can be used for the removal of hair below the eye brow. Strips of material having an inward curve can be used for removal of hair above the eye brow. Different shapes can be used for the removal of hair between the eye brows, etc.

The shaped sheet materials containing the adhesive composition of the present invention can be used for the removal of brow hair very quickly, without the time consuming and painful plucking or messy hot waxing previously used, and the use thereof minimizes brow line errors because of the preshaping to fit any brow line.

The pressure sensitive adhesive composition applied to a face of the sheet material of predetermined size and shape should have the following properties:
1. Sufficient tack or stickiness to adhere firmly to the hair, without, however, adhering firmly to the skin.
2. Sufficient cohesiveness to pull out the hair without the adhesive splitting from the sheet material.
3. Stickiness or tackiness remaining for a sufficient time to permit normal storage.

The adhesive compositions are prepared of (a) a wax or high molecular weight polymer (for cohesion), (b) tackifiers to provide stickiness, (c) softeners such as mineral oil, etc. to adjust the degree of softness and tack, (d) modifiers such as antioxidants to minimize aging.

The composition could also include fillers to control liquid flow, etc.

Most waxes and thermoplastic polymers may be used to make the pressure sensitive adhesive, including natural rubber, butyl rubber, butadiene styrene, block styrene, ethylene vinyl acetate, polyvinyl acetate, ethyl cellulose, natural waxes, etc.

The tackifiers include terpenes, rosin derivatives, cumarone indene, hydrocarbon resins, terpene phenolics, etc.

Softeners include mineral oils, liquid rosin derivatives, lanolin, plasticizers such as dibutyl phthalate, dioctyl phthalate, tricresyl phosphate, etc.

Suitable antioxidents include: 2,2-methylene-bis-(4-methyl-6-tertiary butyl-phenol; 1,3,5-triethyl-2,4,6-tris-(3,5-ditertiary butyl-4-hydroxy benzyl)-benzene; butylated hydroxy anisole; butylated hydroxy toluol; etc.

The adhesive composition may be applied to the shaped sheet material, e.g. cellophane, polyethylene, paper, etc. in any suitable manner.

Thus, for example, all of the ingredients of the adhesive composition can be melted together and applied hot to the face of the shaped sheet material in hot melted condition and there cooled.

Another method of application is the solvent solution method in which the ingredients are dissolved in a mutual solvent or blend of solvents, applied to the sheet material and dried.

Still another method of application is the emulsion method in which the materials are dispersed in an emulsion, applied to the sheet material and dried.

The shaped strips are utilized according to the invention by pressing the shaped sheet material to the area of the body from which it is desired to remove unwanted hair while avoiding application to wanted hair, for example around the eye brow, and pressed firmly onto the skin. The skin is then pulled taut and with a quick motion the strip if peeled off against the direction of the hair growth. This results in removal of the unwanted hair only while the wanted hair remains following the contour of the selected strip.

DESCRIPTION OF PREFERRED EMBODIMENT

The following examples are given to illustrate the present invention. The scope of the invention is not, however, meant to be limited to the specific details of the examples.

EXAMPLE 1

An adhesive composition is prepared of the following components in the proportions given, all amounts being in parts by weight:

| | |
|---|---|
| glycerol ester of hydrogenated rosin | 68.0 |
| block styrene polymer | 10.0 |
| mineral oil | 21.5 |
| antioxidant | .5 |
| | 100.0 |

The above composition is hot melted together and applied to a sheet of clear plastic cut to predetermined shape. After cooling, a paper backing is applied onto the adhesive.

When it is desired to use the strip, the paper backing is removed from the clear plastic coated strip, the plastic strip is applied to the hair that is to be removed, adhesive face against the hair, and pressed firmly onto the skin. The skin is pulled taut and with a quick motion the strip is pulled off from the skin. This results in removal of the hair only on the predetermined portion of the skin covered with the strip. The entire operation is painless.

EXAMPLE 2

An adhesive composition is prepared of the following components:

| | |
|---|---|
| terpene resin softening pt, 85° C. | 65.0 |
| block styrene polymer | 9.0 |
| liquid glycerol ester of hydrogenated rosin | 25.5 |
| antioxidant | .5 |
| | 100.0 |

The composition is applied and used in the same manner as in Example 1.

EXAMPLE 3

An adhesive is prepared of the following components:

| | |
|---|---|
| glycerol ester of hydrogenated rosin | 48.5 |
| pentaerythritol ester of hydrogenated rosin | 20.0 |
| block styrene polymer | 9.0 |
| mineral oil | 22.0 |
| antioxidant | .5 |
| | 100.0 |

This composition is dissolved in a solvent mixture of naptha and toluol and applied to a clear plastic strip of polyethylene. The solvent mixture is evaporated and the further procedure is as set forth in Example 1.

While the invention has been illustrated in particular with respect to specific compositions, it is apparent that variations and modifications of the invention can be made.

What is claimed is:

1. Arrangement for removal of unwanted hair, comprising a plastic sheet material of predetermined shape and size having a pressure sensitive adhesive composition comprising a high molecular weight polymer selected from the group consisting of polymers of natural rubber, butyl rubber, butadiene styrene, block styrene, ethylene vinyl acetate, vinyl acetate, ethyl cellulose and natural waxes in an amount of about 9–10% by weight, a tackifier selected from the group consisting of terpenes, rosin derivatives, coumarone indene, hydrocarbon resins and terpene phenolics in an amount of about 65–68.5% by weight, a softener selected from the group consisting of mineral oil, liquid rosin derivatives, lanolin dibutyl phthalate, dioctyl phthalate and tricresyl phosphate in an amount of about 21.5–25% by weight, and an antioxidant selected from the group consisting of 2,2-methylene-bis(4-methyl-6-tertiary butyl)-phenol, 1,3,5-triethyl-2,4,6-tris-(3,5-ditertiary butyl-4-hydroxy benzyl)-benzene, butylated hydroxy anisole and butylated hydroxy toluol in an amount of about 0.5% by weight applied to a face thereof, said composition adhering firmly to hair but not to skin so that when the same is applied to an area of the body from which it is desired to remove unwanted hair, and subsequently peeled away therefrom, only the unwanted hair is removed.

2. Arrangement according to claim 1 wherein the components of the adhesive composition are glycerol ester of hydrogenated rosin in an amount of 68% by weight, block styrene polymer in an amount of 10% by weight, mineral oil in an amount of 21.5% by weight the antioxidant in an amount of 0.5% by weight.

3. Arrangement according to claim 1 wherein the components of the adhesive composition are terpene resin having a softening point of 85° C. in an amount of 65% by weight, block styrene polymer in an amount of 9% by weight, liquid glycerol ester of hydrogenated rosin in an amount of 25.5% by weight, and the antioxidant in an amount of 0.5% by weight.

4. Arrangement according to claim 1 wherein the components of the adhesive composition are glycerol ester of hydrogenated rosin in an amount of 48.5% by weight, pentaerythritol ester of hydrogenated rosin in an amount of 20% by weight, block styrene polymer in an amount of 9% by weight, mineral oil in an amount of 22% by weight, and the antioxidant in an amount of 0.5% by weight.

* * * * *